United States Patent
Mootz et al.

(10) Patent No.: US 6,881,380 B1
(45) Date of Patent: Apr. 19, 2005

(54) CUP HANDLING SUBSYSTEM FOR AN AUTOMATED CLINICAL CHEMISTRY ANALYZER SYSTEM

(75) Inventors: Frederick E. Mootz, Fort Lee, NJ (US); Carl R. Gebauer, Granite Springs, NY (US); Frank Bakonyi, Danbury, CT (US); Nicolae Dumitrescu, Stamford, CT (US)

(73) Assignee: Bayer Corporation, Tarrytown, NY (US)

( * ) Notice: Subject to any disclaimer, the term of this patent is extended or adjusted under 35 U.S.C. 154(b) by 638 days.

(21) Appl. No.: 09/626,066

(22) Filed: Jul. 26, 2000

Related U.S. Application Data

(62) Division of application No. 09/099,739, filed on Jun. 18, 1998, now Pat. No. 6,117,391.

(51) Int. Cl.[7] .............................................. G01N 29/00
(52) U.S. Cl. ........................ 422/65; 422/63; 422/64; 422/102; 422/104; 436/43; 436/47; 221/298; 221/299
(58) Field of Search .............................. 422/63, 64, 65, 422/99, 102, 104; 436/43, 45, 47, 48; 221/186, 289, 290

(56) References Cited

U.S. PATENT DOCUMENTS

| | | | | |
|---|---|---|---|---|
| 892,688 A | * | 7/1908 | Schrum | 194/251 |
| 2,099,267 A | * | 11/1937 | Hackett | 221/17 |
| 2,529,222 A | * | 11/1950 | Makibbin | 221/122 |
| 2,726,026 A | * | 12/1955 | Gould | 141/104 |
| 3,010,263 A | * | 11/1961 | Carew et al. | 53/435 |
| 3,057,515 A | * | 10/1962 | Loeser et al. | 221/221 |
| 3,186,594 A | * | 6/1965 | Nyblom | 221/299 |
| 3,795,344 A | * | 3/1974 | Falk et al. | 221/116 |
| 3,842,533 A | * | 10/1974 | Mayer | 47/1.01 R |
| 4,260,581 A | * | 4/1981 | Sakurada | 422/65 |
| 4,699,306 A | * | 10/1987 | Smith, Jr. | 227/53 |
| 4,742,937 A | * | 5/1988 | Blom | 221/223 |
| 5,067,308 A | * | 11/1991 | Ward | 53/471 |
| 5,250,440 A | * | 10/1993 | Kelln et al. | 436/48 |
| 5,511,690 A | * | 4/1996 | Calhoun et al. | 221/197 |
| 6,117,391 A | * | 9/2000 | Mootz et al. | 422/65 |

* cited by examiner

*Primary Examiner*—Jill Warden
*Assistant Examiner*—Dwayne K Handy
(74) *Attorney, Agent, or Firm*—Andrew L. Klawitter; Rodman & Rodman

(57) ABSTRACT

The present invention relates to a cup handling subsystem for an automated clinical chemistry analyzer system which includes a nestable sample cup for holding sample mixtures, a cup dispenser mechanism for holding and dispensing a supply of the cups into a sample shuttle for transporting them, and an incubator for controlling the temperature of the cup and its contents. In one embodiment, the cups include a conical lower portion and a cylindrical upper portion having a top flange, a bottom flange and a groove formed therebetween. An apparatus is provided for holding and dispensing a plurality of such cups including a supply tube for holding the cups in a stack wherein the stack has a bottom-most cup and a next-bottom-most cup located above the bottom-most cup. The apparatus also includes an escapement located at a lower end of the supply tube which includes a disk having an aperture formed therein, a first leaf attached to a top side of the disk and a second leaf attached to a bottom side of the disk. The disk is movable between a first position in which the second leaf engages the bottom flange of the bottom-most cup and a second position in which the first leaf is inserted into the groove of the next-bottom-most cup and engages the top flange of the next-bottom-most cup and in which the second leaf no longer engages the bottom flange of the bottom-most cup. In the second position, the bottom-most cup is free to fall through the aperture formed in the disk.

36 Claims, 17 Drawing Sheets

CUP HANDLING SUBSYSTEM FOR AN AUTOMATED CLINICAL CHEMISTRY ANALYZER SYSTEM

This application is a divisional application of U.S. Ser. No. 09/099,739, filed June 18, 1998, now U.S. Pat. No. 6,117,391.

FIELD OF THE INVENTION

The present invention relates to a cup handling subsystem for an automated clinical chemistry analyzer system and specifically a sample cup and an apparatus for holding and individually dispensing a plurality of the sample cups.

BACKGROUND

Automated clinical chemistry analyzer systems that analyze body fluid samples such as treated whole blood, blood serum, blood plasma and urine have been developed with the capability of performing multiple analytical tasks in assembly line fashion as detailed in U.S. Pat. Nos. 5,268,147 and 5,399,497, owned by the assignee hereof. Certain of such systems carry out multiple high speed analytical tests automatically by providing a stream of sample test packets, separated by a gas such as air, that flow through the system in a small diameter fluid conduit. As the stream of sample test packets flows through the system, a number of different tests and measurements are performed.

Automation of analytical testing has many advantages over manual laboratory testing procedures. Improved process control leads to improvements in accuracy and repeatability of the test results. In addition, automated testing can provide results much more rapidly and more cost effectively than manual testing.

Typically, prior to being inserted into the flowing stream for testing, a sample is mixed with one or more prepared reagents or diluents. Diluents such as an aqueous salt solution are used to reduce the analyte concentration of a sample to bring it within the range that can be measured by the system. Reagents are used to generate the chemical reactions necessary for certain testing methods, such as vitamin B12 and folate (folic acid).

Some automated clinical chemistry analyzer systems include a number of different modular subsystems. These may include a pretreatment module in which the sample mixtures described above are prepared and in which certain chemical reactions are generated, and various analytical modules in which the actual testing and analysis of the sample mixtures is performed. Typically, a mechanism, such as a robotic arm, is provided for transporting the sample mixtures between the modules.

SUMMARY OF THE INVENTION

The present invention relates to cup handling subsystem for an automated clinical chemistry analyzer system which includes a nestable cup for holding sample mixtures, a cup dispenser mechanism for holding and dispensing a supply of the cups into an included sample shuttle for transporting them, and an incubator for controlling the temperature of the cup and its contents.

One aspect of the present invention is directed to a first embodiment of a sample cup having a conical lower portion and a cylindrical upper portion having a top flange, a bottom flange and a groove formed therebetween. The center line of the conical and cylindrical portions of the cup are coincident. An alternative embodiment of the sample cup has a conical lower portion and a cylindrical upper portion having a single flange.

Another aspect of the invention is directed to an apparatus for holding and dispensing a plurality of the sample cups having a supply tube for holding the cups in a stack wherein the stack has a bottom-most cup and a next-bottom-most cup located above the bottom-most cup, and an escapement located at a lower end of the supply tube. The escapement includes a disk having an aperture formed therein, a first leaf attached to the top side of the disk and a second leaf attached to the bottom side of the disk.

In one embodiment of the present invention which utilizes the first embodiment of the cup, the escapement is movable between a first position in which the second leaf engages the underside of the bottom flange of the bottom-most cup and a second position in which the first leaf is inserted into the groove of the next-bottom-most cup and engages the top flange of the next-bottom-most cup and in which the second leaf no longer engages the bottom-most cup. In this second position, the bottom-most cup is free to fall through the aperture formed in the disk. In an alternate embodiment of the present invention which utilizes the alternate embodiment of the cup, the second leaf engages the underside of the flange of the bottom-most cup when the escapement is in the first position, and the first leaf engages the underside of the flange of the next-bottom-most cup when the escapement is in the second position.

BRIEF DESCRIPTION OF THE DRAWINGS

Further features and advantages of the present invention will be apparent upon consideration of the following detailed description, taken in conjunction with the following drawings, in which like reference characters refer to like parts, and in which.

DETAILED DESCRIPTION

The present invention relates to a cup handling subsystem for an automated clinical chemistry analyzer system which includes a nestable sample cup for holding sample mixtures, a cup dispenser mechanism for holding and individually dispensing a supply of the cups into an included sample shuttle for transporting them, and an incubator for controlling the temperature of the cup and its contents.

Figure 1:
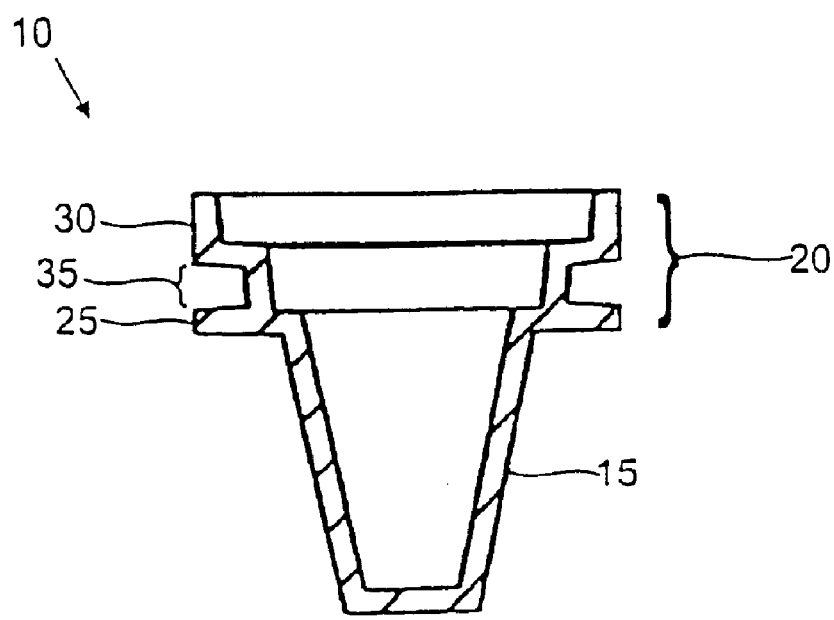
FIG. 1 is a section view of a sample cup according to an aspect of the present invention.
Figure 1A:
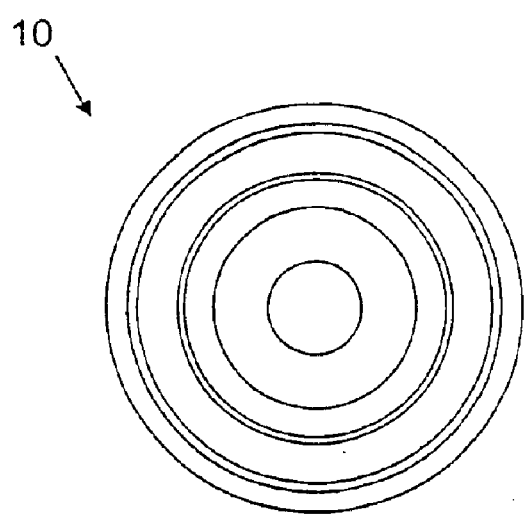
FIG. 1A is a top view of the sample cup shown in FIG. 1.
Figure 2:
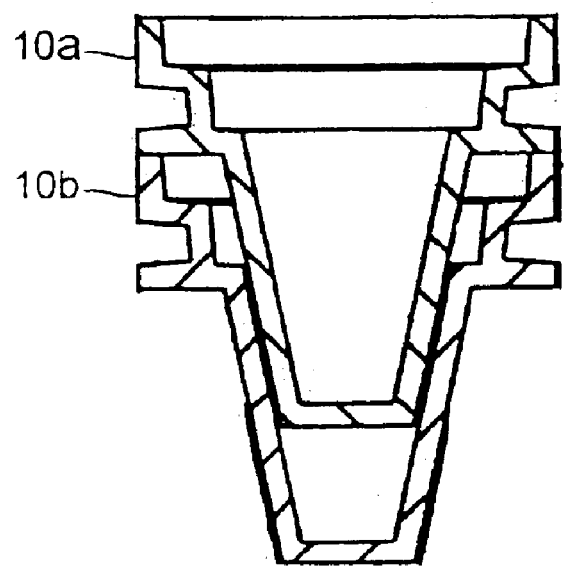
FIG. 2 is a sectional view of two cups, as shown in FIG. 1, nested together.

Referring to FIG. 1, a section view of the cup 10 is shown. FIG. 1A shows a top view of the cup 10 shown in FIG. 1. As shown in FIG. 1, the cup 10 has a conical lower portion 15 and a cylindrical upper portion 20. FIG. 2 is a section view of two cups, 10a and 10b, nested together. Preferably, the height of cylindrical upper portion 20 is chosen so that the cups will not tumble or roll within the supply tube 45 to be described below. In the preferred embodiment, the minimum height of cylindrical upper portion 20 that will prevent tumbling is 6 mm, which results in a usable volume of the cup on the order of 100 μl, although the cup 10 can hold considerably more liquid. In the embodiment shown, the cups nest in a 3:1 ratio with a pitch on the order of 6 mm. The greater the nesting ratio, the more stable the stack of cups when handled by a user outside the supply tube. Suitable ranges include from 1.5:1 to 6:1 and pitches between 2 and 20 mm. In addition, clearance between the conical surfaces of the nested cups is small enough, preferably between 0.1 and 1 mm, more preferably on the order of 0.2 mm, to provide stability to the stack of cups while being handled and yet large enough to prevent wedging of the cups together. Referring again to FIG. 1, the cylindrical upper portion 20 of the cup 10 includes a bottom flange 25, a top flange 30 and a groove 35 between the bottom flange 25 and the top flange 30. The height of the top flange 30 is large enough to be readily gripped by the gripper arm of a robot (not shown) used to transport and manipulate the cups 10 within and between the various subsystems of the automated clinical chemistry analyzer system. Suitable dimensions of the top flange 30 include 1 to 15 mm. Also, as noted above, the total height of the cylindrical upper portion 20 is such that the cup 10 cannot tumble or become un-nested when inserted into an appropriate diameter supply tube of the cup dispenser mechanism to be described in detail below.

Figure 1B:
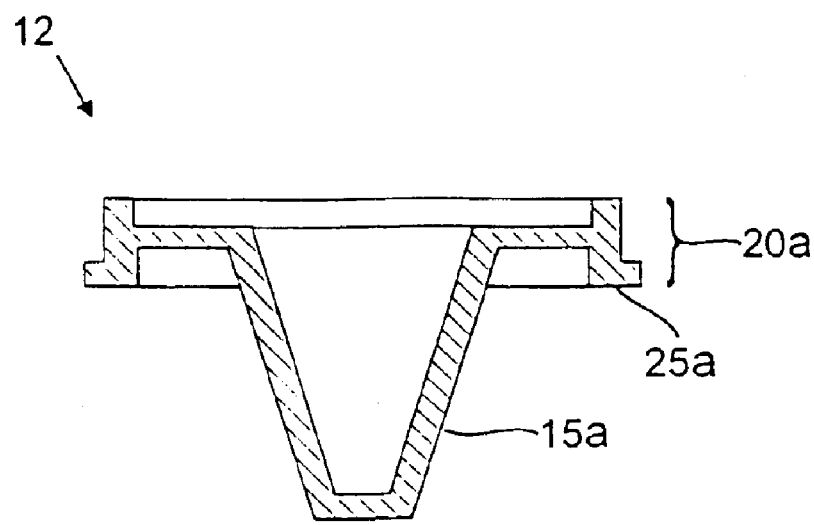
FIG. 1B is a section view of a sample cup according to a further aspect of the present invention.

Referring to FIG. 1B, an alternate embodiment of a sample cup, designated as 12, is shown. Like the embodiment shown in FIG. 1, the embodiment shown in FIG. 1B has a conical lower portion 15a and a cylindrical upper portion 20a. However, unlike the cup 10 shown in FIG. 1 which has bottom flange 25, top flange 30 and groove 35, the cup shown in FIG. 1B has only a single flange 25a. Thus, when cups 12 are nested within one another, the flanges 25a of adjacent cups form a groove therebetween.

Figure 3:
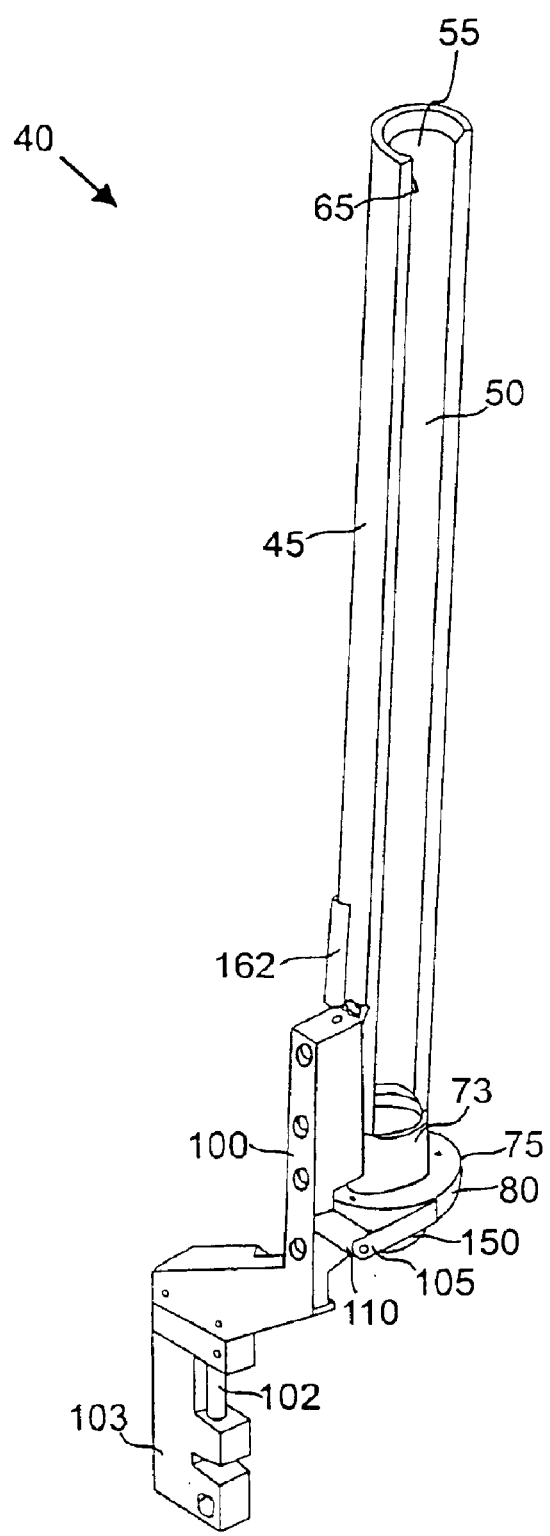
FIGS. 3 and 4 are isometric views of the cup dispenser mechanism according to an aspect of the present invention.
Figure 4:
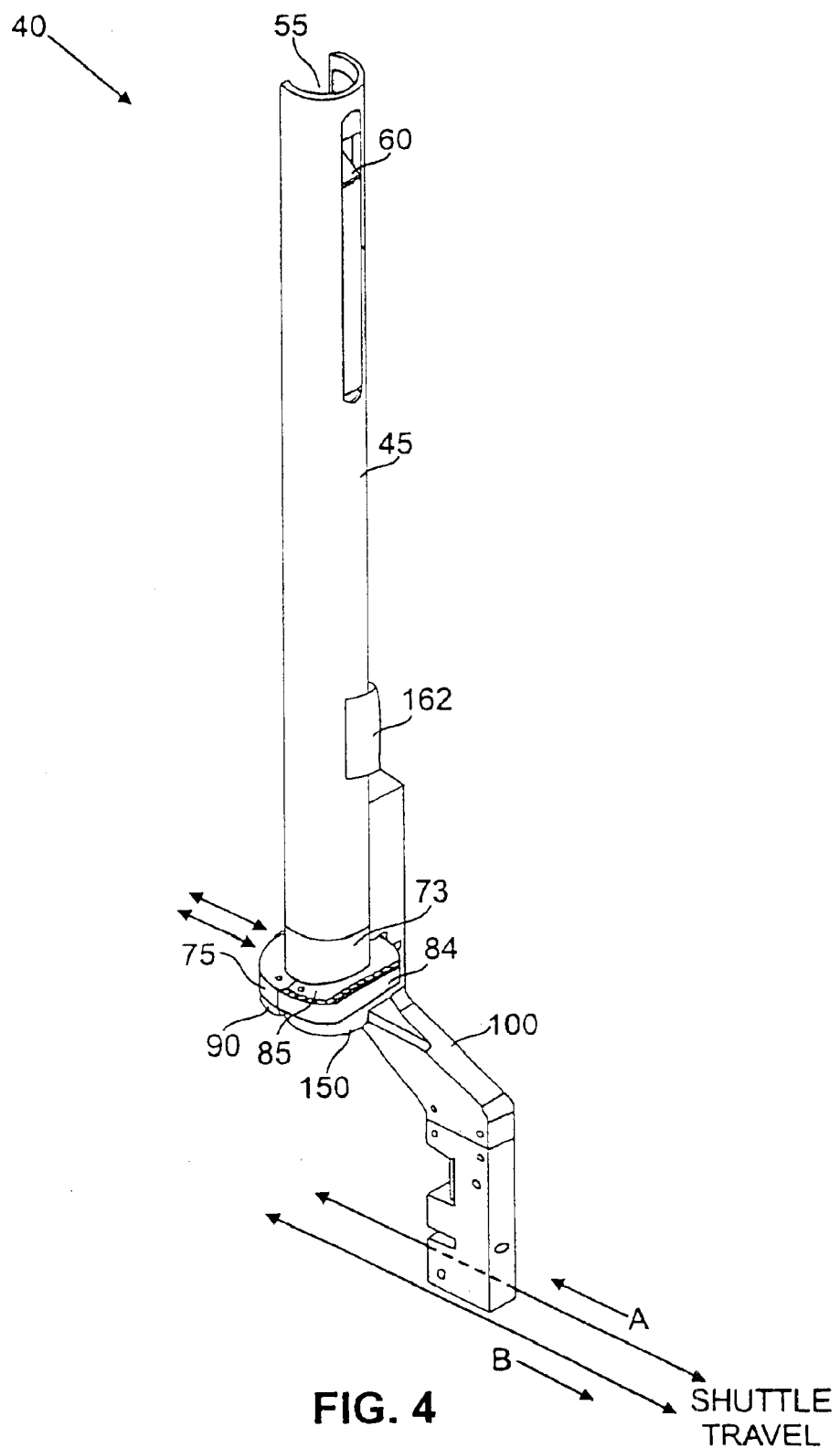

Referring to FIGS. 3 and 4, perspective views of cup dispenser mechanism 40 are shown. Cup dispenser mechanism 40 includes cylindrically shaped supply or feeder tube 45 having an opening 50 along the length thereof such that the supply tube 45 takes on the shape of a C-channel. The supply tube 45 is arranged to hold a nested stack of cups 10 by placing the nested stack of cups 10 inside the supply tube 45 through upper opening 55. An operator can thus easily place the cups 10 into the supply tube 45 and either slide them down or allow them to fall into position. The slot in the front of the supply tube 45 provides visibility to confirm the presence, number, and orientation of cups in the supply tube 45.

Figure 5:
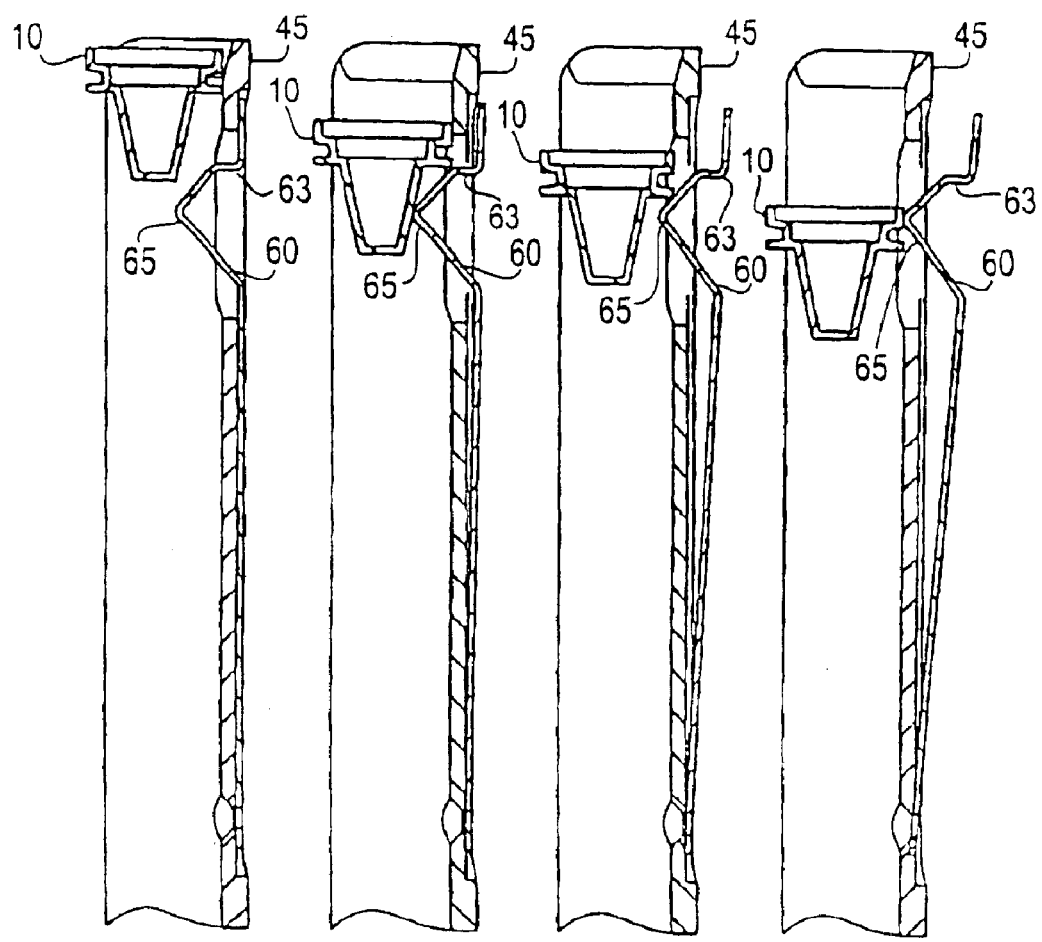
FIG. 5 is a diagram showing the guide spring of the cup dispenser mechanism shown in FIGS. 3 and 4 and illustrating the operation thereof when the cup is inserted conical lower portion first.
Figure 6:
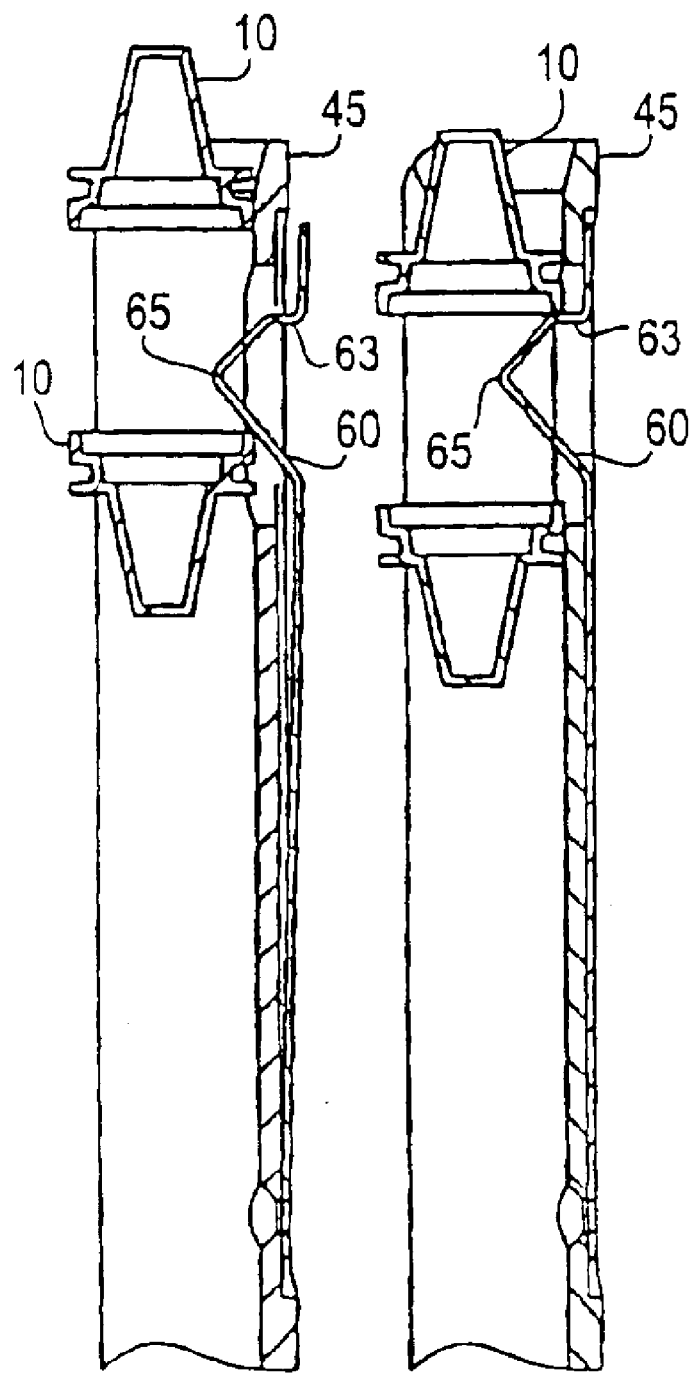
FIG. 6 is a diagram showing the guide spring of the cup dispenser mechanism shown in FIGS. 3 and 4 and illustrating the operation thereof when the cup is inserted cylindrical upper portion first.

To ensure that the nested stack of cups 10 is inserted into the supply tube 45 in the proper orientation, i.e., such that the conical lower portion 15 of the bottom most cup 10 in the nested stack enters the supply tube 45 first and is facing downwards (small end of the cone is pointing downward), the supply tube 45 is provided at the top thereof with a guide spring 60 having a substantially flat shoulder 63, also called a cup stop, and an angular member 65, also called a cup follower, which protrudes into the inner-channel of supply tube 45 as shown in FIG. 3. As illustrated in FIG. 5, if the nested stack of cups 10 is inserted into the supply tube 45 in the proper orientation, i.e., conical lower portions first, the conical lower portion 15 of the bottom most cup 10 will push on the cup follower 65 and push the cup stop 63 and the remainder of the guide spring 60 out of the way as shown by the arrows. Thus, the nested stack of cups 10 is able to be slid or is able to fall into place. If, however, the nested stack of cups 10 is inserted into the supply tube 45 in the improper orientation, i.e., with the cylindrical upper portion 20, first, then, as illustrated in FIG. 6, the guide spring 60 will not be pushed out of the way because the cylindrical upper portion 20 will get hung up on the cup stop 63 of the guide spring 60. As a result, the cups will be prevented from travelling further and it will be obvious to the operator that the cup orientation was incorrect.

Figure 7:
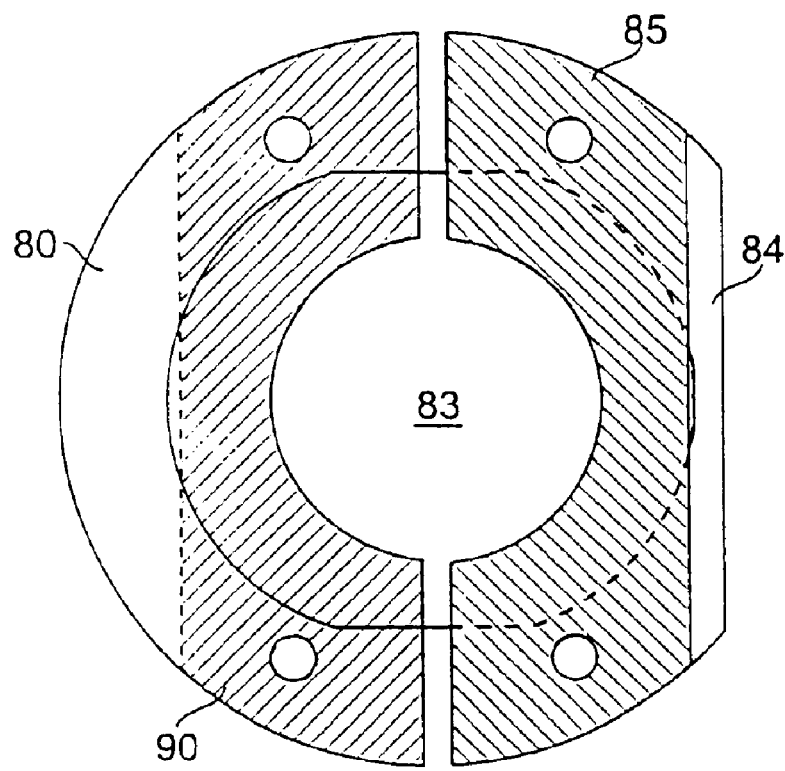
FIG. 7 is a top view of the escapement according to an aspect of the present invention.
Figure 8:
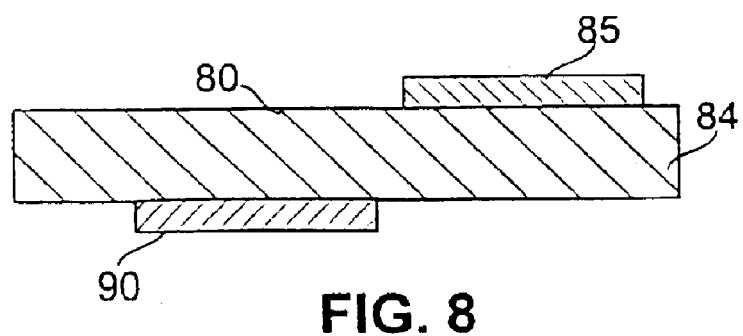
FIG. 8 is front view of the escapement according to an aspect of the present invention.

Referring again to FIGS. 3 and 4, the cup dispenser mechanism includes a cylindrically shaped escapement housing 73 affixed to the lower portion of supply tube 45. The escapement housing 73 houses escapement 75. As shown in FIGS. 7 and 8, the escapement 75 includes disk-shaped member 80 having an aperture 83 therein and a flat face 84. Attached to the disk-shaped member 80 on the top side thereof is top leaf 85, and attached to the disk-shaped member 80 at the bottom side thereof is bottom leaf 90. Because FIG. 7 is a top-view of the disk-shaped member 80, the portion of bottom leaf 90 obscured by the disk-shaped number 80 is shown in dotted lines. The thickness bottom leaf 90 is chosen such that it will not fit into grooves 35 of cup 10, the thickness of top leaf 85 is chosen such that it will fit into groove 35 of cup 10. The significance of this feature will become more apparent when the operation of the escapement 75 is described in detail below.

Referring to FIG. 3, supply tube 45 is mounted to support 100. The cup dispenser mechanism 40 can be mounted to the support 100 in such a way to allow easy removal of the cup dispenser mechanism 40. Easy removal facilitates maintenance of the cup dispensing mechanism and allows access to other areas around and behind the cup dispensing mechanism. Specifically, as shown in FIG. 3, pins 102 (only one pin is shown) are interference fit into holes in support 100 so as to be securely attached thereto. Pins 102 are also clearance fit into holes in mounting assembly 103 which is attached to the shuttle assembly (not shown) of the subsystem. In addition, mounting assembly 103 is provided with a spring loaded ball plunger (not shown) for engaging the securing pins 102 when they are fit into the holes of the mounting assembly 103. As a result, the cup dispenser mechanism 40 is able to be firmly secured in place in mounting assembly 103 through operation of pins 102 and the spring loaded ball plunger, but can also be readily removed with a sharp pull in the vertical direction.

Disk-shaped member 80 is movably attached to support 100 by spring 105 and pin 110. Thus, because of the flexible nature of spring 105 and because the diameter of aperture 83 is larger than the diameter of supply tube 45 and the escapement housing 73, disk-shaped member 80 having leaves 85 and 90 is able to move laterally with respect to the longitudinal axis of supply tube 45 as shown by the arrows in FIG. 4. Furthermore, the escapement housing 73 is provided with apertures on opposite sides thereof which are aligned with leaves 85 and 90, respectively. Thus, as the disk-shaped member 80 moves laterally with respect to the supply tube 45, the leaves 85 and 90 are able to move inside of the escapement housing 73.

Figure 9A:
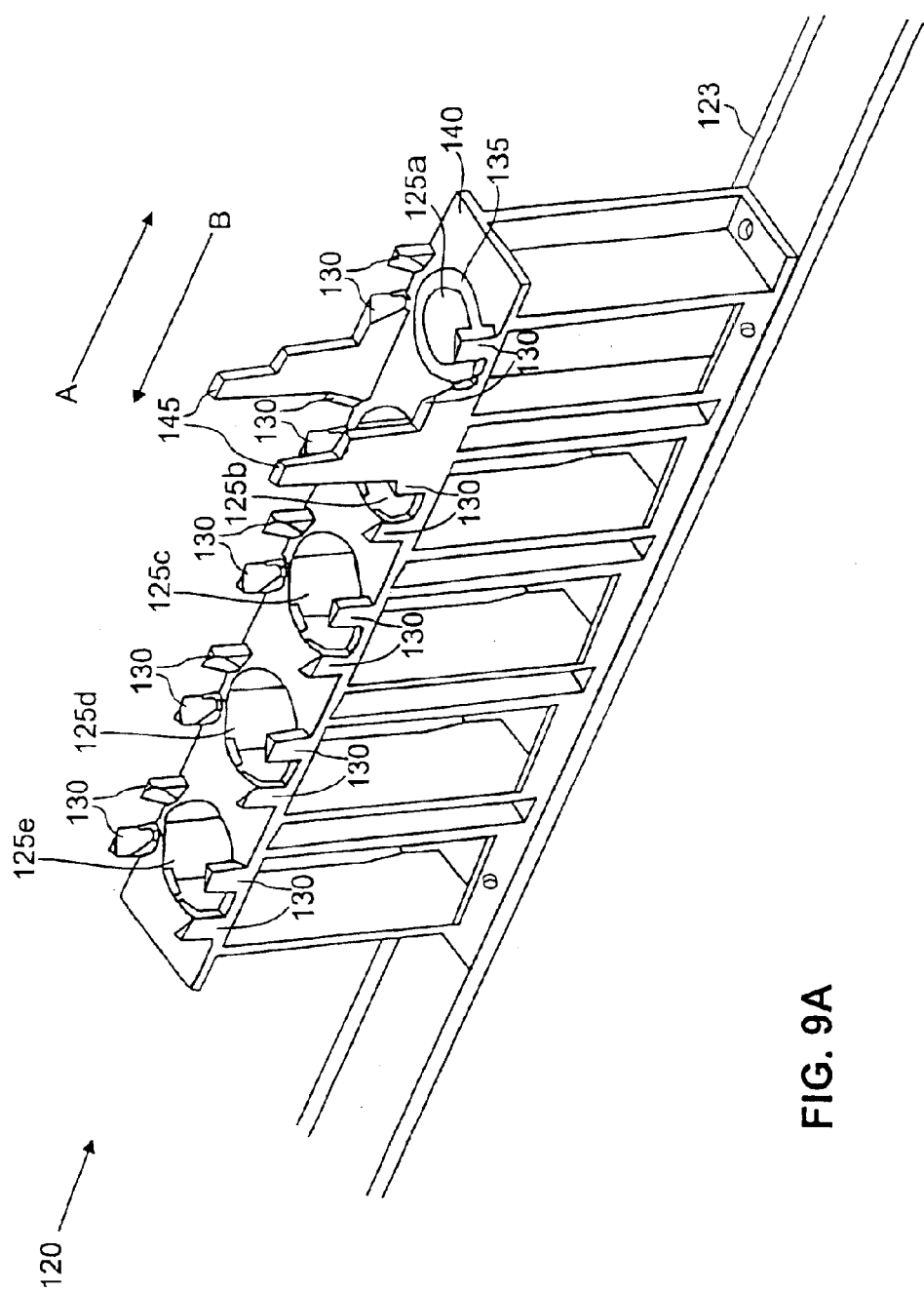
FIGS. 9A and 9B are isometric views of the sample shuttle according to aspects of the present invention.
Figure 9B:
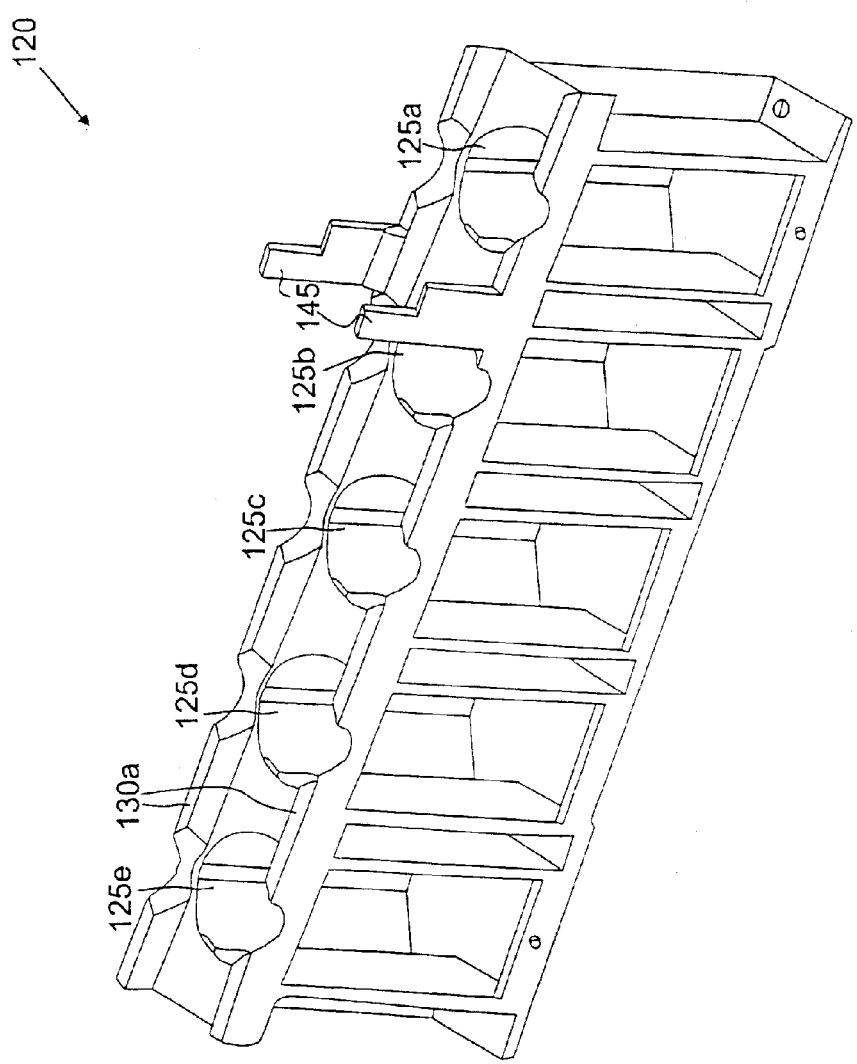

The cup handling subsystem of the present invention is also provided with sample shuttle 120, a first embodiment of which is shown in FIG. 9A. With conventional software control, the sample shuttle 120 is able to automatically move back and forth along track 123 beneath supply tube 45 in the directions shown in FIG. 4. As shown in FIG. 9A, the sample shuttle 120 includes a plurality of sample positions 125a through 125e. Sample positions 125a through 125e are shaped to receive and hold a sample receptacle such as cups 10 or 12 or a standard test tube. Furthermore, each sample position 125 is provided with lead-in pins 130, which facilitate seating of cups 10 or 12 when they are placed in the sample position 125 by, for example, the robot (not shown). In addition, as shown in FIG. 9A, sample position 125a is provided with cylindrical insert 135 having an inside diameter which is slightly larger than the diameter of the top of the conical lower portion 15 of cup 10 or 12. By top it is meant that part of the conical lower portion 15 or 15a that is closest to bottom flange 25 of cup 10 or flange 25a of cup 12. When a cup 10 or 12 is dropped into sample position 125a from supply tube 45 via the escapement, as will be described in detail below, the conical lower portion 15 of the cup 10 or 15a of cup 12 provides a lead-in to the cylindrical insert 135, whose diameter is smaller than that of sample positions 125b through 125e. In addition, the top surface of the cylindrical insert 135, which is flush with the top surface 140 of the sample shuttle 120, provides stable support for the cylindrical upper portion 20 of the cup 10 or 20a of cup 12. Sample shuttle 120 is also provided with trigger or actuation pins 145 between sample positions 125a and 125b, whose purpose, as is described in detail below, is to acuate the escapement 75 to allow a cup 10 or 12 to drop from supply tube 45 into sample position 125a. FIG. 9B shows an alternate embodiment of the sample shuttle 120 in which the individual lead-in-pins 130 are replaced by a single integrated lead-in-wall 130a on each side thereof.

The operation of escapement 75 in connection with sample shuttle 120 will now be described. As can be seen in FIGS. 10 through 13, which are section views of the escapement housing 73 and escapement 75, disk-shaped member 80 moves laterally with respect to the longitudinal axis of the supply tube 45 among various positions as has been described briefly above. The lateral movement is accomplished by the interaction of sample shuttle 120 with escapement 75. Specifically, the sample shuttle 120 moves along the track 123 in direction A shown in FIGS. 4 and 9A such that actuation pins 145 engage flat face 84 of disk-shaped member 80, thereby pushing it against the return tension provided by spring 105 and moving it laterally in direction A. Similarly, when the sample shuttle 120 reverses direction and moves along the track 123 in direction B shown in FIGS. 4 and 9A, the disk-shaped member moves laterally in direction B by the return force of spring 105 and eventually the actuation pins 145 disengage with flat face 84 of disk-shaped member 80.

Referring again to FIGS. 3 and 4, the cup dispenser mechanism includes a cylindrically shaped escapement housing 73 affixed to the lower portion of supply tube 45. The escapement housing 73 houses escapement 75. As shown in FIGS. 7 and 8, the escapement 75 includes disk-shaped member 80 having an aperture 83 therein and a flat face 84. Attached to the disk-shaped member 80 on the top side thereof is top leaf 85, and attached to the disk-shaped member 80 at the bottom side thereof is bottom leaf 90. Because FIG. 7 is a top-view of the disk-shaped member 80, the portion of bottom leaf 90 obscured by the disk-shaped number 80 is shown in dotted lines. The thickness bottom leaf 90 is chosen such that it will not fit into grooves 35 of cup 10, the thickness of top leaf 85 is chosen such that it will fit into groove 35 of cup 10. The significance of this feature will become more apparent when the operation of the escapement 75 is described in detail below.

The function of escapement 75 is to permit only the bottom-most cup 10 or 12 located within supply tube 45 to drop from the bottom 150 of escapement housing 73 into sample position 125a of the sample shuttle 120, while the remaining cups 10 or 12 within supply tube 45 are held in place. FIGS. 10 through 13 show the various stages of operation of the escapement 75, in connection with the embodiment of the cup 10 shown in FIG. 1, which accomplish this function.

Figure 10:
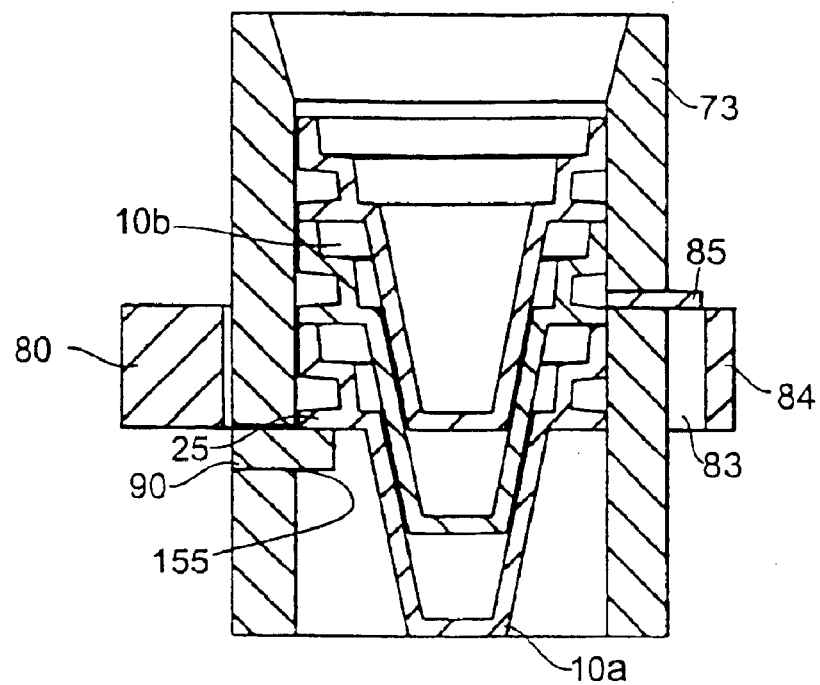
FIGS. 10 through 13 are section views of the escapement in its housing which illustrate the different operating positions of its cup dispensing function.

FIG. 10 shows the escapement 75 in the full return position prior to the beginning of the sequence for releasing the bottom-most cup, shown in the Fig. as 10a. In this position, the acuation pins 145 of the sample shuttle 120 have not yet engaged flat face 84 of disk-shaped member 80. As shown in FIG. 10, top leaf 85 is located outside of the interior of escapement housing 73 and bottom leaf 90 is located within the interior of escapement housing 73, having entered escapement housing 73 through aperture 155. Thus, bottom leaf 90 engages bottom flange 25 of cup 10a, thereby supporting the entire nested stack of cups within the supply tube 45.

Figure 11:
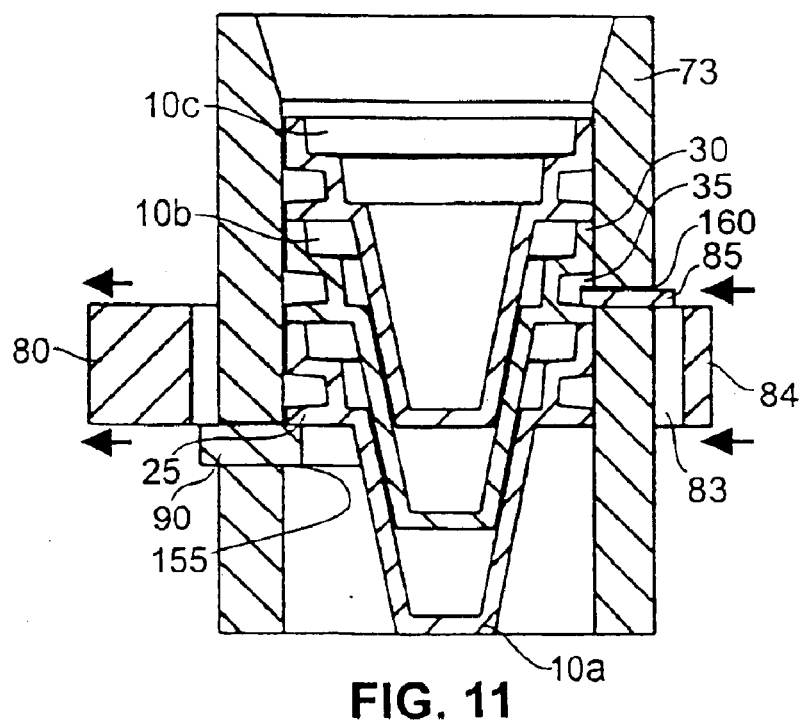

Referring to FIG. 11, as the acuation pins 145 of sample shuttle 120 engage flat face 84, disk-shaped member 80 is pushed against the tension of spring 105 and is moved laterally as shown by the arrows. As a result, bottom leaf 90 is also moved laterally, although still engaging the bottom flange 25 of bottom-most cup 10a (i.e., the stack of cups is still supported by leaf 90). At the same time, top leaf 85 has entered the interior of escapement housing 73 through aperture 160. The top leaf 85 has also entered the groove 35 of cup 10b, which is the next cup above bottom-most cup 10a, but has not yet engaged the top flange of cup 10b.

Figure 12:
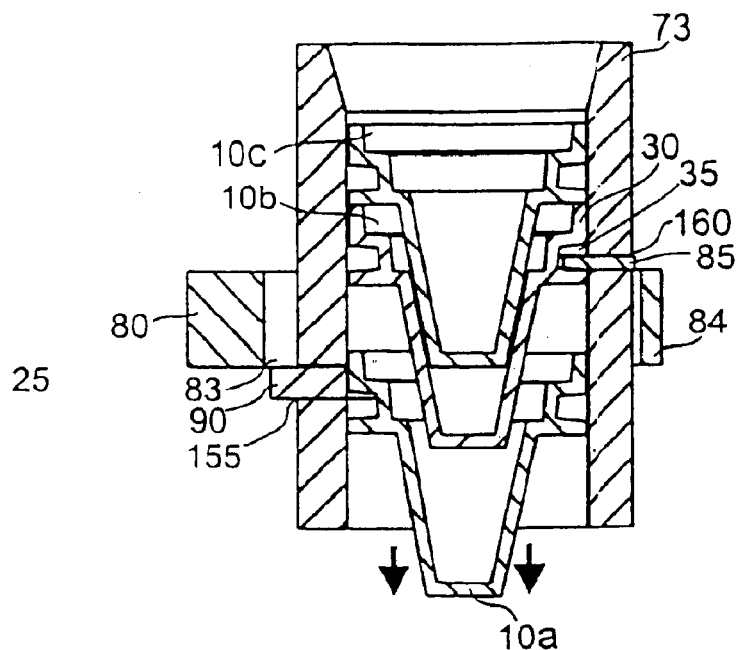

FIG. 12 shows the full forward position of the escapement 75 in which the bottom-most cup 10a is no longer supported by leaf 90 and is thus free to fall into sample position 125a of the sample shuttle 120. At this point, the sample shuttle 120 has moved as far in direction A as possible. As the bottom-most cup 10a falls, the remaining cups 10 above bottom-most cup 10a fall together until the upper flange 30 of cup 10b engages top leaf 85, thereby supporting the entire stack up cups 10 above cup 10b.

Figure 13:
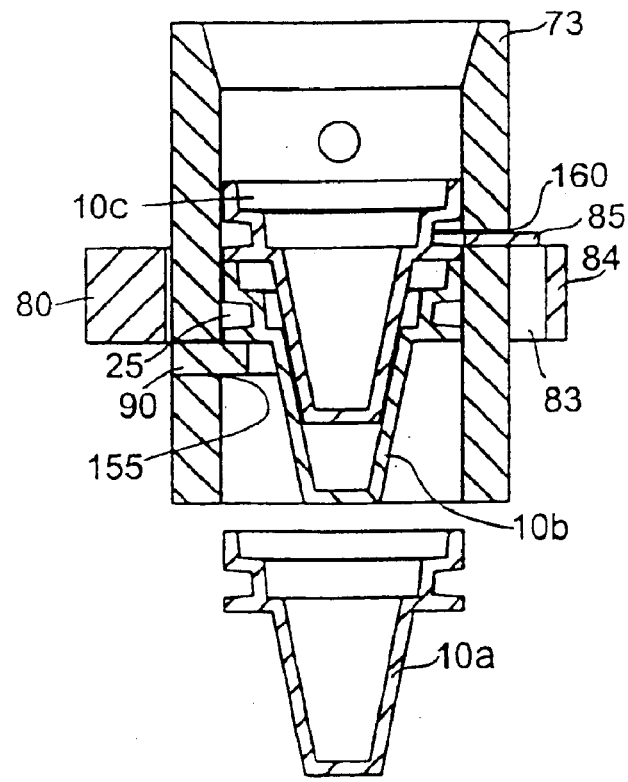

After the bottom-most cup 10a has fallen free from the supply tube 45, the sample shuttle 120 moves in direction B. FIG. 13 shows the escapement 75 after it has returned to the full return position. As can be seen in FIG. 13, top leaf 85 has exited the interior of escapement housing 73 and bottom leaf 90 engages bottom flange 25 of cup 10b, which is now the bottom-most cup in the stack, thereby supporting the entire stack. In this full return position, the acuation pins 145 of sample shuttle 120 no longer engage flat face 84.

As noted above, the thickness of the bottom leaf 90 is chosen such that it is larger than the width of groove 35 of cups 10. In other words, bottom leaf 90 cannot fit inside groove 35. This feature eliminates the danger of the bottom leaf 90 mistakenly entering groove 35 at anytime during the operation of the escapement as described herein.

The above described procedure is repeated each time it is desired to load a new cup 10 into the sample holder 120 at sample position 125a. Thus, the cups 10 can automatically and sequentially be dispensed one at a time from supply tube 45 using an existing transport device and without the need of additional electromechanical devices and additional software control to the system. Once a cup is dispensed into sample holder 120, the cup can be filled with a sample and the various mixtures described above can be selectively created.

When the embodiment of cup 12 shown in FIG. 1B is used, the operation of the escapement mechanism is substantially as described above. Specifically, in the full return position, the bottom leaf 90 engages the flange 25a of the bottom-most cup 12, thereby supporting the entire stack of cups 12 (when cups 10 are utilized, the bottom leaf 90 engages the bottom flange 25 of the bottom-most cup). However, as the disk-shaped member 80 is moved laterally, instead of the top leaf 85 moving into groove 35 as was the case with cups 10, the top leaf 85 moves into position under the flange 25a of the next cup 12 above the bottom-most cup so as to engage the flange 25a of that next cup and thus support the stack of cups 12 when the bottom-most cup 12 falls.

Referring to FIG. 4, cup dispenser mechanism 40 is provided with a reflective optical sensor 162 mounted on the supply tube 45 for sensing when the number of cups within the supply tube 45 has fallen below a certain level, for example 10. In particular, the reflective optical sensor 162 is mounted adjacent a hole provided in the supply tube 45 and includes an LED for emitting light through the hole and a receptor for detecting any light that is reflected back. Thus, when cups are stacked within the supply tube 45 at or above the level of the hole, the light emitted by the reflective optical sensor 162 is reflected and detected by the receptor. When, however, the level of the cups drops below the hole, the light emitted by the reflective optical sensor 162 is not reflected, and thus the reflective optical sensor 162 detects a low cup condition and alerts the operator.

In addition, a reflective optical sensor (not shown) is mounted adjacent the escapement 75, for example on the support 100 or on the shuttle assembly (not shown), for confirming that a cup 10 or 12 has been dispensed into the shuttle 120. Specifically, as described above, the reflective optical sensor includes an LED for emitting light toward the sample position 125a and a receptor for detecting any light that is reflected back. Thus, if a cup 10 or 12 is present in sample position 125a, the receptor will detect reflected light and the sensor will indicate that a cup has been dispensed. If, however, a cup is not dispensed into sample position 125a, the receptor will not detect reflected light and the sensor will indicate that a cup has not been dispensed. The reflective optical sensor can also be used before the shuttle 120 actuates the escapement 75 to confirm that a cup 10 or 12 is not already located in sample position 125a to avoid a jamming of cup dispenser mechanism 40.

Furthermore, as noted above, for certain samples it may be desirable to mix the sample with a reagent or reagents to create a chemical reaction. For many such reactions, it is necessary to heat the sample and reagent mixture to a specified temperature for a specified time period. For this purpose, incubator 165, shown in FIGS. 14 through 19, is provided. Thus, when a reaction is desired, a cup 10 or 12 can be dispensed into sample position 125a of sample shuttle 120 as described above. The sample and the reagent can be dispensed into the cup 10 or 12, and then the cup 10 or 12 containing the mixture can be transferred by the robot (not shown) to the incubator 165 for heating.

Figure 14:
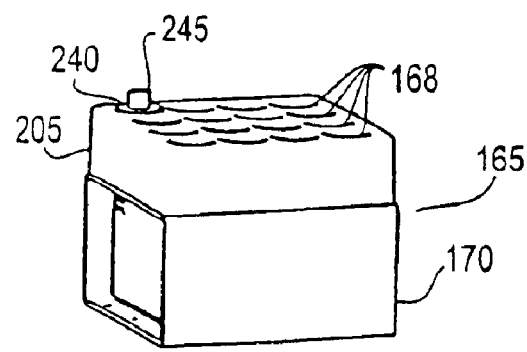
FIG. 14 is an isometric view of the incubator according to an aspect of the present invention.
Figure 15:
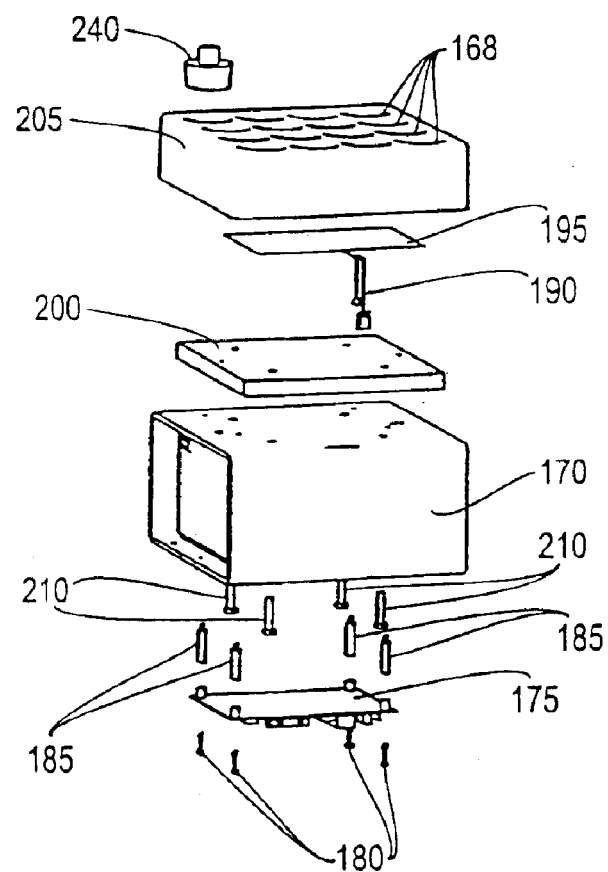
FIG. 15 is an exploded isometric view of the incubator shown in FIG. 14.
Figure 16:
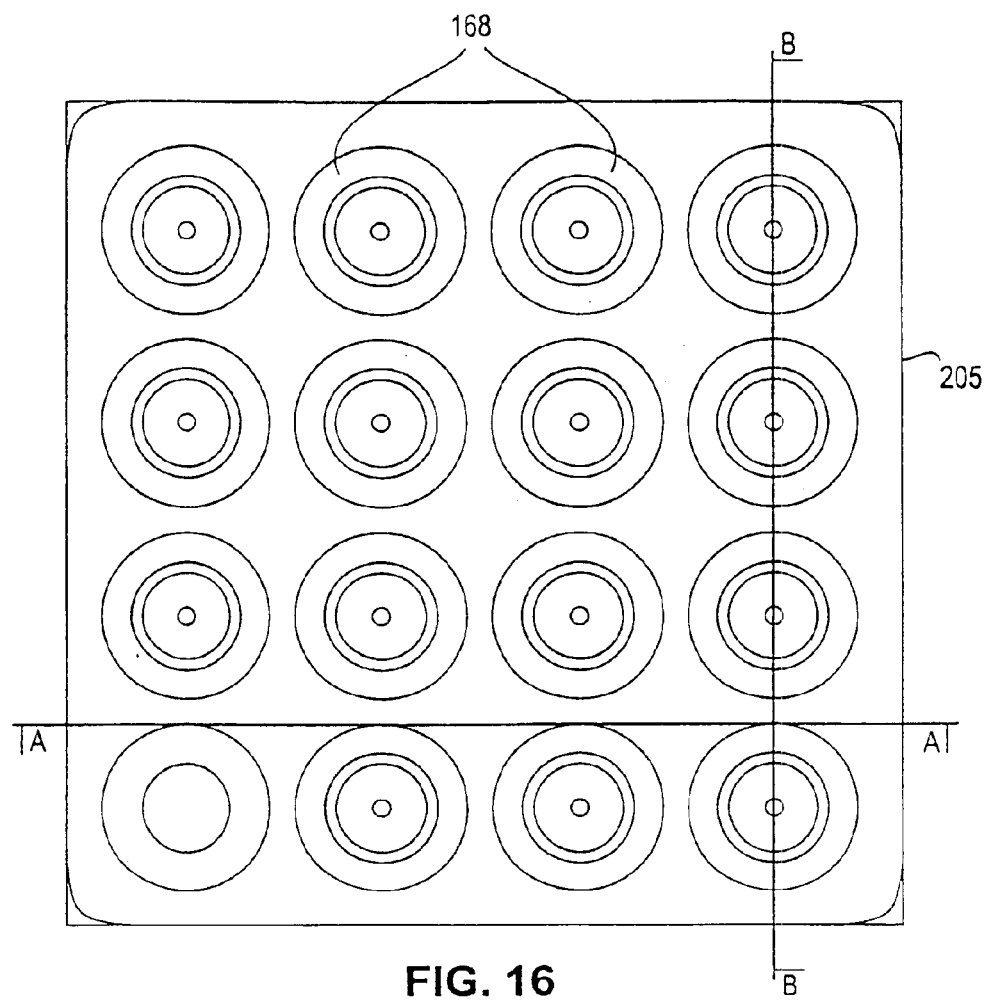
FIG. 16 is a top view of the incubator shown in FIG. 14.
Figure 17:
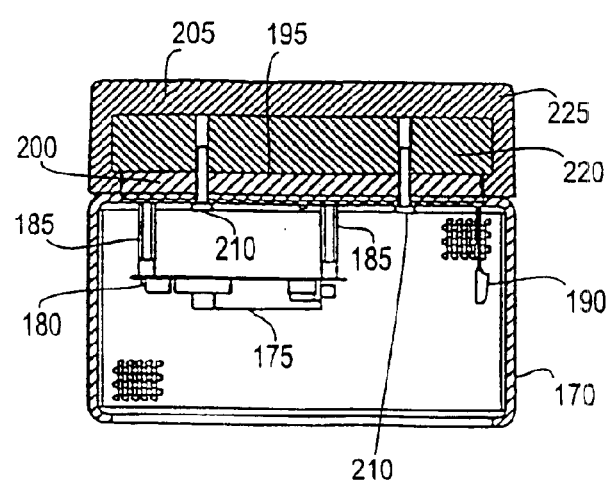
FIG. 17 is a section view of the incubator taken along line A—A shown in FIG. 16.
Figure 18:
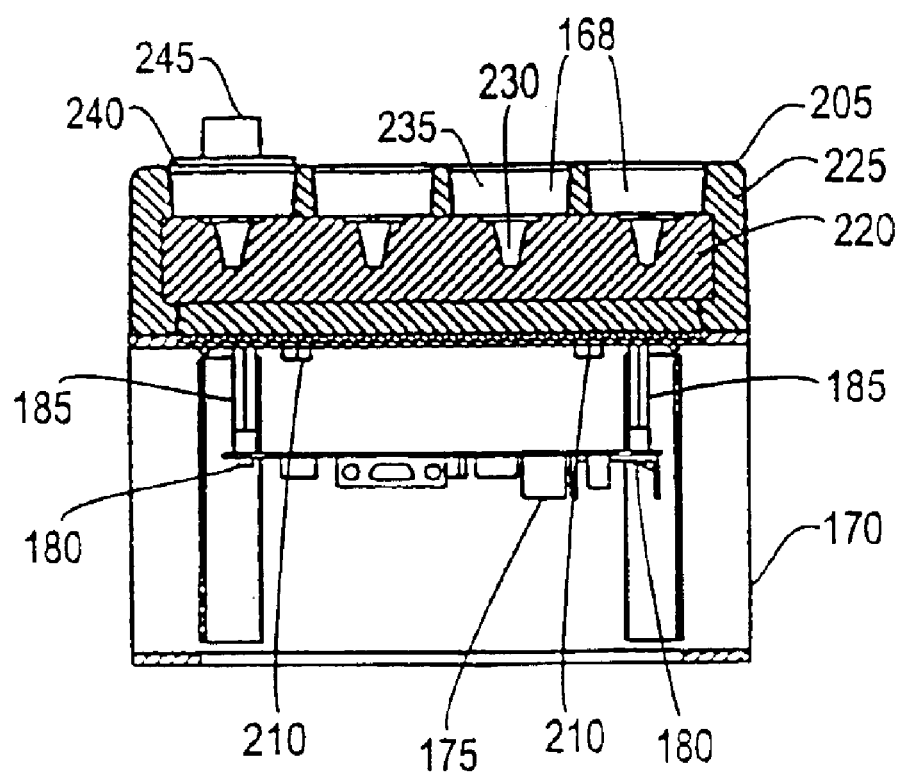
FIG. 18 is a section view of the incubator taken along lines B—B shown in FIG. 16.

Referring to FIGS. 14 and 15, an isometric view and an exploded isometric view, respectively, of incubator 165 are provided. As can be seen in FIGS. 14 and 15, incubator 165 includes a number of cup holding positions 168, sixteen for example, which are designed to receive and hold cups 10 or 12. FIG. 16 shows a top view of incubator 165 which illustrates the layout of cup holding positions 168. FIGS. 17 and 18 are section views of the incubator 165 taken along lines A—A and B—B, respectively, shown in FIG. 16.

As shown in FIGS. 17 and 18, incubator 165 includes support 170 to which a temperature controller 175, such as a PID or proportional integrating derivative controller, an example of which is a Thermologic brand controller, is attached by screws 80 and standoffs 185. Incubator 165 also includes a temperature sensor 190, such as a thermistor, heater 195, pad insulator 200, and heat sink/insulation assembly 205, all of which are attached to support 170 by screws 210. Heat sink/insulation assembly 205 includes heat sink 220 surrounded by insulation shell 225. Such a heating assembly as just described is well known in the art and thus its operation will not be described in greater detail herein.

As shown in FIG. 18, cup holding positions 168 include a lower portion 230 and an upper portion 235. The lower portion 230 is formed in heat sink 220 and is shaped so as to readily receive and hold cups 10 or 12. In particular, lower portion 230 has a conical shape which closely matches conical lower portion 15 of cup 10 or 15a of cup 12. Upper portion 235 is formed in insulation shell 235 and is provided with a diameter which is large enough to allow the gripper arm of the robot to fit into sample position 168 and pick-up and place cups 10 or 12 by gripping the top flange 30 of cups 10 or the cylindrical upper portion 20a of cup 12 above flange 25a.

Incubator 165 is also provided with insulating covers 240 shown in FIGS. 14, 15 and 18, which are placed into cup holding positions 168 when a cup 10 or 12 is placed therein for temperature control. Insulating covers 240 are readily grippable by the robot gripper arm by means of handle 245. In a preferred embodiment, incubator 165 is provided with at least one less, and most preferably exactly one less, insulating cover 240 than the number of cup holding positions 168. In the example shown in FIGS. 14 through 18 no more than fifteen, and most perferably exactly fifteen, insulating covers 240 would be provided. Thus, in this preferred embodiment, there will always be at least one uncovered cup holding position 168 to which the robot can move a particular insulating cover 240 when it is necessary to access a particular cup 10 or 12.

Incubator 165 thus provides a temperature-controlled environment for samples undergoing a reaction prior to further analysis. Cup 10 or 12 and its contents are brought to a specified temperature for a specified time by heat transfer through heat sink 220. Thermal contact is made to conical lower portion 15 of cup 10 or 115*a* of cup 12 via the matching conical shape of lower portion 230 of cup holding position 168. Cup 10 or 12 is protected from varying ambient temperature and humidity conditions by cover 240, which stays over cup 10 or 12 during its entire stay in the incubator 165. Covers 240 also help to minimize evaporation.

Figure 19:
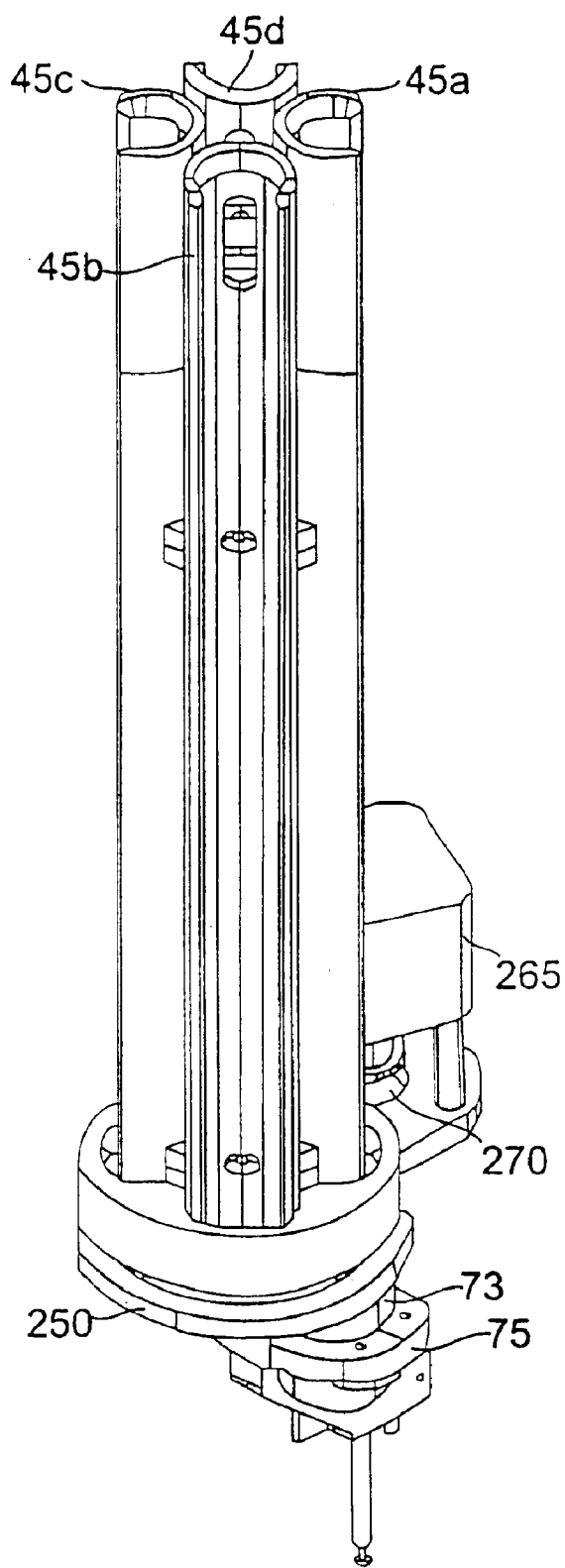
FIG. 19 is an isometric view of the cup dispenser mechanism with a rotable set of supply tubes according to an alternate embodiment of the present invention.
Figure 20:
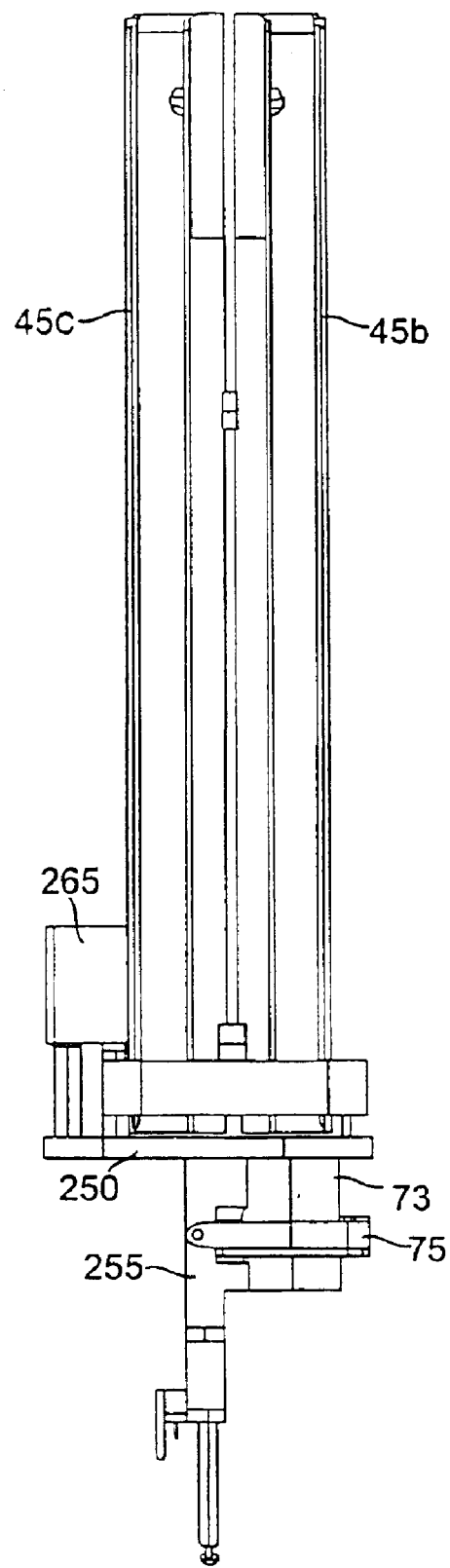
FIGS. 20 and 21 are side and top views, respectively, of the alternate embodiment of the cup dispenser mechanism shown in FIG. 19.
Figure 21:
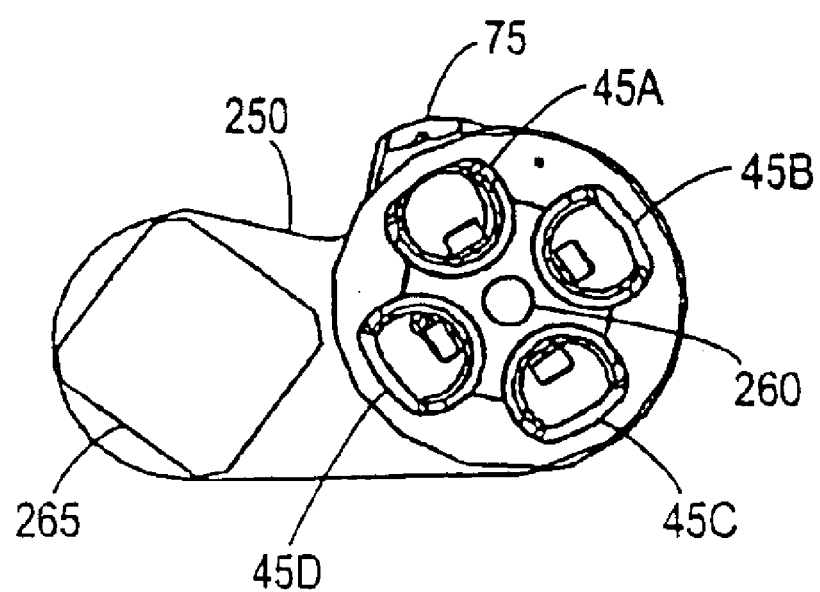

Referring to FIG. 19, an alternate embodiment of the present invention is shown in which, instead of a single supply tube 45, multiple supply tubes are provided on a rotating turret. In FIG. 19, supply tubes 45*a*, 45*b*, 45*c* and 45*d* are shown for illustrative purposes, although more or less may be provided without departing from the scope of the present invention. FIGS. 20 and 21 are side and top views, respectively, of the embodiment shown in FIG. 19. Thus, the rotating turret arrangement allows supply tube 45*a* to be in use, supply tubes 45*b* and 45*c* to be filled and available, and supply tube 45*d* to be accessible for refill.

As shown in FIGS. 19 and 20, the rotating turret assembly includes a stationary platform 250 attached to support 255. Attached to the stationary platform 250 are escapement housing 73 and escapement mechanism 75, whose structure and operation are as described above. Furthermore, rotatably affixed above stationary platform 250 are supply tubes 45*a*, 45*b*, 45*c* and 45*d*. In the example shown in FIGS. 19 through 21, the supply tubes 45*a*, 45*b*, 45*c* and 45*d* are provided so that they rotate through 360° around pivot point bearing 260. Furthermore, the supply tubes 45*a*, 45*b*, 45*c* and 45*d* are separated from one another by 90°, although the tubes 45 need not be equidistantly spaced around the turret. In the embodiment shown in FIGS. 19 through 21, stepper motor 265 coupled to a belt (not shown) and pulley 270 are provided for selectively rotating the turret assembly and thus selectively positioning the tubes 45 over the escapement mechanism 75. Other means for rotating the turret assembly are also possible. For example, the shuttle 120 moving along track 123 can be used to selectively rotate the turret assembly.

Thus, as shown in FIG. 19, supply tube 45*a* (the "in use" tube) is centered over the escapement mechanism 75. The nested cups 10 or 12 in supply tube 45*a* extend through a hole in the stationary plate 250 and into the escapement mechanism 75. The escapement mechanism 75 is actuated by the sample shuttle 120 as described above. When supply tube 45*a* is completely depleted of cups 10, the turret can rotate to bring supply tube 45*b* over the escapement mechanism 75. Once emptied and rotated away from the escapement mechanism 75, supply tube 45*a* is available to be refilled. Another rotation will place supply tube 45*c* over the escapement mechanism 75 and place supply tube 45*d* next in line to be used, and so on.

One skilled in the art will appreciate that the present invention can be practiced by other than the described embodiments, which are presented for purposes of illustration and not of limitation.

We claim:

1. An apparatus for holding and dispensing a plurality of cups, each of said cups having a conical lower portion and a cylindrical upper portion having a top flange, a bottom flange, and a groove formed therebetween, comprising:
   a supply tube having a lower end and an interior suitable for holding said cups in a stack, said stack having at least a bottom-most cup and a next-bottom-most cup located above said bottom-most cup; and
   an escapement located adjacent the lower end of said supply tube, said escapement including a disk having a top side, a bottom side and an aperture formed therein, a first leaf fixedly attached to the top side of said disk and a second leaf fixedly attached to the bottom side of said disk;
   wherein said escapement is moveable between a first position in which said second leaf engages the bottom flange of said bottom-most cup and a second position in which said first leaf is inserted into the groove of said next-bottom-most cup and engages the top flange of said next-bottom-most cup and in which said second leaf no longer engages the bottom flange of said bottom-most cup such that said bottom-most cup falls through said aperture formed in said disk.

2. An apparatus according to claim 1, further comprising a support, wherein said supply tube is fixedly attached to said support and wherein said escapement is moveably attached to said support by a spring.

3. An apparatus according to claim 1, further comprising means for moving said escapement between said first position and said second position.

4. An apparatus according to claim 1, further comprising a sample shuttle having a plurality of sample holding positions and at least one actuation pin, wherein said escapement is moveable in a first direction between said first position and said second position, wherein said sample shuttle is moveable in said first direction and said at least one actuation pin engages said escapement and moves said escapement from said first position to said second position.

5. An apparatus according to claim 4, wherein one of said sample holding positions is located directly beneath said supply tube when said escapement is moved to said second position.

6. An apparatus according to claim 5, wherein said sample holding position located directly beneath said supply tube is provided with a cylindrical insert, and wherein when a cup falls through said aperture formed in said disk, said conical lower portion of said cup is guided by said cylindrical insert.

7. An apparatus according to claim 6, wherein said cylindrical insert has an inside diameter slightly larger than a largest diameter of said conical lower portion measured at a position adjacent said cylindrical upper portion.

8. An apparatus according to claim 1, further comprising means for ensuring that said cups are inserted into said supply tube conical lower portion first.

9. An apparatus according to claim 1, wherein said supply tube further comprises a spring having an angular portion and a cup stop which protrude into said interior of said supply tube, wherein said angular portion and said cup stop are pushed out of said interior to allow said cups to slide past said spring when said cups are inserted into said supply tube conical lower portion first, and wherein said angular portion and said cup stop remain in said interior to prevent said cups from sliding past said spring when said cups are inserted into said supply tube cylindrical upper portion first.

10. An apparatus according to claim 1, wherein said second leaf has a thickness and wherein said thickness is chosen such that said second leaf will not fit into said groove.

11. An apparatus according to claim 1, further comprising an incubator having a temperature controller, a temperature sensor, a heater, and an insulated heat sink, said incubator having N cup holding positions and up to N-1 insulating covers which fit over said cup holding positions.

12. An apparatus according to claim 11, wherein said cup holding positions include a conical lower portion adapted to receive said conical lower portion of said cups, and a cylindrical upper portion having a diameter larger than a diameter of said cylindrical upper portion of said cups.

13. An apparatus according to claim 12, wherein when said cups are inserted into said cup holding positions, said conical lower portions of said cups are in thermal contact with said conical lower portions of said cup holding positions.

14. An apparatus according to claim 1, wherein said supply tube has a C-shaped cross section.

15. An apparatus according to claim 1, wherein said supply tube further comprises at least two supply tubes mounted on a rotatable turret.

16. An apparatus according to claim 15, wherein each of said supply tubes has a lower end and wherein said turret can be rotated to selectively position a selected one of said lower ends of said supply tubes over said escapement.

17. An apparatus according to claim 1, wherein said bottom flange of said cups has a bottom surface, and wherein said top flange of said cups has a top surface, and wherein a distance between said bottom surface and said top surface is chosen such that a plurality of said cups can nest within one another in a ratio between 1.5 to 1 and 6 to 1.

18. An apparatus according to claim 1, wherein said bottom flange of said cups has a bottom surface and wherein said top flange of said cups has a top surface, and wherein a distance between said bottom surface and said top surface is between 2 mm and 20 mm such that said cup cannot tumble when placed inside said supply tube.

19. A cup handling subsystem for an automated clinical chemistry analyzer system, comprising:

a plurality of cups, each of said cups having a conical lower portion and a cylindrical upper portion having a top flange, a bottom flange, and a groove formed therebetween;

a supply tube having a lower end and an interior suitable for holding said cups in a stack, said stack having at least a bottom-most cup and a next-bottom-most cup located above said bottom-most cup;

an escapement located adjacent the lower end of said supply tube, said escapement including a disk having a top side, a bottom side and an aperture formed therein, a first leaf attached to the top side of said disk and a second leaf attached to the bottom side of said disk, wherein said escapement is moveable between a first position in which said second leaf engages the bottom flange of said bottom-most cup and a second position in which said first leaf is inserted into the groove of said next-bottom-most cup and engages the top flange of said next bottom-most cup and in which said second leaf no longer engages the bottom flange of said bottom-most cup such that said bottom-most cup falls through said aperture formed in said disk; and an incubator.

20. A cup handling subsystem according to claim 19, wherein said incubator comprises a temperature controller, a temperature sensor, a heater, and an insulated heat sink.

21. A cup handling subsystem according to claim 20, wherein said incubator has N cup holding positions and up to N-1 insulating covers which fit over said cup holding positions.

22. A cup handling subsystem according to claim 21, wherein said cup holding positions include a conical lower portion adapted to receive said conical lower portion of said cups, and a cylindrical upper portion having a diameter larger than a diameter of said cylindrical upper portion of said cups.

23. A cup handling subsystem according to claim 22, wherein when said cups are inserted into said cup holding positions, said conical lower portions of said cups are in thermal contact with said conical lower portions of said cup holding positions.

24. A cup handling subsystem according to claim 19, further comprising a support, wherein said supply tube is fixedly attached to said support and wherein said disk is moveably attached to said support by a spring.

25. A cup handling subsystem according to claim 19, further comprising means for moving said disk between said first position and said second position.

26. A cup handling subsystem according to claim 19, further comprising a sample shuttle having a plurality of sample holding positions and at least one actuation pin, wherein said escapement is moveable in a first direction between said first position and said second position, wherein said sample shuttle is moveable in said first direction and said at least one actuation pin engages said escapement and moves said disk from said first position to said second position.

27. A cup handling subsystem according to claim 26, wherein one of said sample holding positions is located directly beneath said supply tube when said escapement is moved to said second position.

28. A cup handling subsystem according to claim 27, wherein said sample holding position located directly beneath said supply tube is provided with a cylindrical insert, and wherein when a cup falls through said aperture formed in said disk, said conical lower portion of said cup is guided by said cylindrical insert.

29. A cup handling subsystem according to claim 28, wherein said cylindrical insert has an inside diameter slightly larger than a largest diameter of said conical lower portion measured at a position adjacent said cylindrical upper portion.

30. A cup handling subsystem according to claim 19, wherein said supply tube further comprises a spring having an angular portion and a cup stop which protrude into said interior of said supply tube, wherein said angular portion and said cup stop are pushed out of said interior to allow said cups to slide past said spring when said cups are inserted into said supply tube conical lower portion first, and wherein said angular portion and said cup stop remain in said interior to prevent said cups from sliding past said spring when said cups are inserted into said supply tube cylindrical upper portion first.

31. A cup handling subsystem according to claim 19, wherein said second leaf has a thickness and wherein said thickness is chosen such that said second leaf will not fit into said groove.

32. A cup handling subsystem according to claim 19, wherein said supply tube further comprises at least two supply tubes mounted on a rotable turret.

33. A cup handling subsystem according to claim 32, wherein each of said supply tubes has a lower end and wherein said turret can be rotated to selectively position a selected one of said lower ends of said supply tubes over said escapement.

34. A cup handling subsystem according to claim 19, wherein said bottom flange of said cups has a bottom surface, and wherein said top flange of said cups has a top surface, and wherein a distance between said bottom surface and said top surface is chosen such that a plurality of said cups can nest within one another in a ration between 1.5 to 1 and 6 to 1.

35. A cup handling subsystem according to claim 19, wherein said bottom flange of said cups has a bottom surface and wherein said top flange of said cups has a top surface, and wherein a distance between said bottom surface and said top surface is between 2 mm and 20 mm such that said cup cannot tumble when placed inside said supply tube.

36. An apparatus for holding and dispensing a plurality of cups, each of said cups having a conical lower portion and a cylindrical upper portion having a top flange, a bottom flange, and a groove formed therebetween, comprising:

a plurality of supply tubes mounted on a rotatable turret, each supply tube having a lower end and an interior suitable for holding said cups in a stack, said stack having at least a bottom-most cup and a next-bottom-most cup located above said bottom-most cup; and an escapement located adjacent the lower end of a selected one of said supply tubes, said escapement including a disk having a top side, a bottom side and an aperture formed therein, a first leaf attached to the top side of said disk and a second leaf attached to the bottom side of said disk;

wherein said escapement is moveable between a first position in which said second leaf engages the bottom flange of said bottom-most cup and a second position in which said first leaf is inserted into the groove of said next-bottom-most cup and engages the top flange of said next-bottom-most cup and in which said second leaf no longer engages the bottom flange of said bottom-most cup such that said bottom-most cup falls through said aperture formed in said disk.

* * * * *

UNITED STATES PATENT AND TRADEMARK OFFICE
CERTIFICATE OF CORRECTION

PATENT NO. : 6,881,380 B1
DATED : April 19, 2005
INVENTOR(S) : Frederick E. Mootz et al.

It is certified that error appears in the above-identified patent and that said Letters Patent is hereby corrected as shown below:

Column 4,
Line 47, change "number" to -- member --.

Column 6,
Lines 6-22, delete "Referring again...detail below".
Line 64, change "up" to -- of --.

Column 8,
Line 28, change "80" to -- 180 --.
Line 42, change "235" to -- 225 --.

Column 9,
Line 2, change "115a" to -- 15a --.

Column 12,
Line 51, change "rotable" to -- rotatable --.
Line 62, change "ration" to -- ratio --.

Signed and Sealed this

First Day of November, 2005

JON W. DUDAS
*Director of the United States Patent and Trademark Office*